United States Patent [19]
Starrett et al.

[11] Patent Number: 6,146,880
[45] Date of Patent: Nov. 14, 2000

[54] METHODS FOR LYOPHILIZING AND USING ERICOID MYCORRHIZAL FUNGI

[75] Inventors: Mark C. Starrett, Burlington, Vt.; Frank A. Blazich, Raleigh, N.C.; Steven R. Shafer, Raleigh, N.C.; Larry F. Grand, Raleigh, N.C.

[73] Assignees: The United States of America as represented by the Secretary of Agriculture, Washington, D.C.; North Carolina State University, Raleigh, N.C.

[21] Appl. No.: 09/026,437

[22] Filed: Feb. 19, 1998

[51] Int. Cl.$^7$ .................................................... C12N 1/04
[52] U.S. Cl. ...................... 435/260; 435/254.1; 435/911; 504/117
[58] Field of Search ............................... 435/260, 254.1, 435/911; 504/117

[56] References Cited

U.S. PATENT DOCUMENTS 4,702,923  10/1987  Tokumaru et al. .
5,360,607  11/1994  Eyal et al. .

OTHER PUBLICATIONS

Pons et al., *Les Mycorhizes: biologie et utilisation*, Dijon, 5–6 mai. 1982, pp. 345–349.
Barnes et al., *J. Environ. Hort.*, vol. 4(4), pp. 109–111, Dec. 1986.
Litten et al., *Can. J. Bot.*, vol. 70, pp. 2202–2206, 1992.
Berta et al., *Tree Physiology*, vol. 15, pp. 281–293, 1995.
Cardinale et al., *Allionia*, vol. 33, pp. 87–92, 1995.
Starrett et al, *J. Environ. Hort.*, vol. 11(4), pp. 191–195, Dec. 1993.
Raymond Chee, *American Nurseryman*, vol. 161(10), pp. 42–47, May 1995.
Pertot et al., *European Journal of Applied Microbiology*, vol. 4, pp. 289–294, 1977.
Marx et al., *Canadian Journal of Microbiology*, vol. 22, pp. 338–341, 1976.
Von G. Bazzigher, *Phytopath. Z.*, vol. 45, pp. 53–56, 1962.
D. J. Bagyaraj, In: *Beneficial Fungi and Their Utilization*, M.C. Nair et al.–Eds., pp. 59–84, 1986.
Jeffries et al., *Handbook of Applied Mycology, Soil and Plants*, vol. 1, 1991.
Y. Dalpe, In: Proceedings of the Seventh North American on Mycorrhiza, D.M. Sylvia et al.–Eds., p. 279, 1987.
John G. Torrey, *Can. J. For. Res.*, vol. 22, pp. 1815–1823, 1992.
Starrett et al., *SNA Research Conference*, vol. 40, pp. 266–267, 1995.
Starret et al., *SNA Research Conference*, vol. 41, pp. 239–242, 1996.

*Primary Examiner*—Leon B. Lankford, Jr.
*Attorney, Agent, or Firm*—M. Howard Silverstein; John D. Fado; Gail E. Poulos

[57] ABSTRACT

The present invention is directed to a method for preserving mycorrhizal fungi for long-term storage using lyophilization. This enables use of the fungi for growing and acclimatizing micropropagated plants. The invention is especially useful for preserving mycorrhizal ericoid fungi for long-term storage and use in a soilless medium for growing micropropagated ericaceous plants.

13 Claims, No Drawings

METHODS FOR LYOPHILIZING AND USING ERICOID MYCORRHIZAL FUNGI

BACKGROUND OF THE INVENTION

1. Field of the Invention

The present invention relates to a method of lyophilizing ericoid mycorrhizal fungi, lyophilized ericoid mycorrhizal fungi per se, and a system for using the lyophilized ericoid mychorrhizal fungi, especially for micropropagated Ericaceous plants. The present invention also relates to any ericaceous plants propagated with the lyophilized ericoid fungi.

2. Description of the Related Art

Species in the Ericaceae are indigenous to almost every region of the world. These plants often thrive on otherwise unproductive sites because they develop specialized mycorrhizal associations common to most, if not all, ericaceous plants (Jackson and Mason, Mycorrhiza. Studies in Biology, no. 159, 1984). Many ericaceous plants are found on acidic, nutrient-poor soils high in organic matter. Association with an ericoid mycorrhizal fungus is often necessary for survival in such conditions. Ericoid mycorrhizal fungi can degrade organic residues produced by ericaceous plants themselves, thus providing mineral nutrients otherwise unavailable to their host plants (Read, In: Frontiers in Mycology: Honorary and General Lectures from the Fourth International Mycological Congress, Hawksworth-ed., 1990).

Micropropagation of ericaceous plants is a widely used method for propagation. Many media have been described to improve root development of the host plant and to increase the potential for synthesis of a mycorrhizal association between fungal inoculum and host. Moore-Parkhurst and Englander (Mycologia, Volume 73, 994–997, 1981) disclosed a method that included a paper bridge support over a liquid medium for synthesis of mycorrhizae between *Hymnenoscyphus ericae* and *Rhododendron maximum* (rosebay rhododendron). Similarly, Douglas et al. (Can. J. Bot., Volume 67, 2206–2212, 1989) disclosed the same system with a slightly modified liquid medium for inoculation of Rhododendron with *Oidiodendron maius* Barron. This method was effective in promoting growth of both plants and fungi. However, the procedure is very labor intensive and has limited commercial applications.

Pearson and Read (New Phytol., Volume 72, 371–379, 1973) developed a less complicated method for synthesis of ericoid mycorrhizae in aseptic culture. In this procedure, a layer of sterilized soil was placed on top of a water agar base which allowed a simple, effective method for promoting development of ericoid mycorrhizae with roots of host plants.

*Hymenoscyphus ericae* (Read) Korf and Kernan [syn. *Pezizella ericae* Read] is a widespread ericoid mycorrhizal fungus (Moore-Parkhurst and Englander, 1991, supra; Read, Can. J. Bot., Volluem 61, 381–419, 1983). Mycorrhizal associations with this fungus have been demonstrated with *Calluna vulgaris* (L.) Hull [heather, (Read, Trans. Brit. Mycol. Soc., Volume 63, 381–419, 1974)], *Rhododendron chapmanii* Gray [Chapman's rhododendron, (Barnes and Johnson, 1986, supra)], *Rhododendron maximum* L. (Duddridge and Read, Can. J. Bot., Volume 60, 2345–2356, 1982), *Vaccinium angustrifolium* Ait. [lowbush blueberry, (Couture et al., New Phytol., Volume 95, 315–380, 1983)] and *V. corymobosum L. (Lareau,* 1985, supra). Several fungi in the genus, Oidiodendron Robak, also form mycorrhizal associations with plants in the Ericaceae (Couture et al., 1983, supra; Currah et al., Can. J. Bot., Volume 71, 1481–1485, 1993, Dalpé, New Phytol., Volume 103, 391–396, 1986; Douglas et al., Can. J. Vot., Volume 67, 2206–2212, 1989).

*Oidiodendron griseum* Robak is a species that forms mycorrhizae with *V. angustifolium* (Couture, 1983, supra; Dalpé, supra) and *V. corymbosum* (Couture et al., 1983, supra; Lareau, 1985, supra). A related species, *Oidiodendron maius* Barron, was isolated from roots of Rhododendron X 'Pink Pearl' and formed typical ericoid mycorrhizae when reassociated with rooted microsnoots of this cultivar (Douglas et al., 1989, supra). Other species of Oidiodendron forming ericoid mycorrhizae have been reported (Currah et al., 1993, supra; Dalpé, Can. J. Bot., Volume 69, 1712–1714, 1991; Stoyke and Currah, Can. J. Bot., Volume 69, 347–352, 1991; Xiao and Berch, Mycologia, Volume 84, 470–471, 1992).

A micropropagation protocol developed by Anderson (Proc. Intl. Plant Prop. Soc., Volume 28, 135–139, 1978) is currently used for rapid, commercial propagation of rhododendrons and includes an agar-solidified medium without addition of soil. A soilless medium may be used for direct rooting of microshoots following production of microshoots by this protocol, or microshoots may be induced to root in vitro in the agar medium. Micropropagated rhododendrons are often rooted ex vitro in a peat:vermiculite (V:V) medium (Barnes and Johnson, J. Environ. Hort., Volume 4, 109–111, 1986; Smagula and Litten, Acta Hort., volume 241, 110–114, 1989). However, Pieris D. Don. (andromeda) requires a root initiation phase in vitro (Pennell, The Plantsman, Volume 12, 120–125, 1990). Starrett et al. (J. Environ. Hort., Volume 11, 191–195, 1993) included an in vitro rooting step in a procedure developed for micropropagation of *Pieris fioribunda* (mountain andromeda).

Often, the greatest losses during micropropagation occur during plantlet acclimatization to greenhouse conditions (Preece and Sutter, In: Micropropagation, 71–93, Debergh and Zimmerman-ed., 1991). Typically, 10% of micropropagated plants in the Ericaceae either die or do not attain market standards during acclimatization, causing significant commercial losses (Lemoine et al., Agroniomie, Volume 12, 881–885, 1992). Unfortunately, ericaceous plants have exhibited mixed responses when inoculated with ericoid mycorrhizal fungi during micropropagation (Barnes and Johnson, 1986, supra; Berta and Gianinazzi-Pearson, In: Physiological and Genetic Aspects of Mycorrhizae, 673–676, Gianinazzi-Pearson and Gianinazzi-ed., 1986; Lareau, Acta Hort., volume 165, 197–205, 1985; Smagula and Litten, 1989, supra; Starrett et al., Proc. Southern Nurserymen's Assoc. Res. Conf., 40th Annu. Rpt., 266–268, 1995).

Fungal cultures are often preserved on fungal slants (Ainsworth, IN: Introduction to the History of Mycology, Cambridge University Press, New York, 359, 1976). Repeated transfers and long-term storage of active fungal cultures can result in physiological or morphological variation such as loss of pathogenicity. Inadvertent selection of atypical parts of a culture for transfer can also lead to stock cultures that differ from the orginal wild type. Risk of contamination and expense in labor and time requirements also increase with transfers of active cultures (Smith and Onions, The Preservation and Maintenance of Living Fungi. Commonwealth Mycol. Inst., Kew, Richmond, United Kingdom, 1983). Ectomycorrhizal fungi often die or lose their symbiotic ability after several years of repeated subculturing on agar media (Marx and Daniel, Can. J. Microbiol., Volume 22, 338–341, 1976).

A method of lyophilization of fungal cultures was proposed (Raper and Alexander, Mycologia, Volume 37, 499–525, 1945) to reduce losses common to transfer and storage. Long-term storage is especially important to preservation of mycorrhizal fungi. However, little information is available on potential applications of lyophilization for preservation of mycorrhizal fungi. Lyophilization has been effective only for species of arbuscular mycorrhizal fungi with thick-walled spores (Dalpé, IN: Proc. Seventh North Amer. Conf. on Mycorrhiza, 279, 1987, Sylvia et al.-eds.). Spores and hyphae of seven species of vesicular-arbuscular (VA) mycorrhizal fungi remained viable for eight years in dry storage in a vacuum (L-drying) (Tommerup, In: Proceedings of the 6th North American Conference on Mycorrhizae, 87, 1985). However, L-drying involves temperatures greater than zero degrees centegrade. Mature nonsporulating agar cultures of pathogenic fungi were preserved successfully by freeze-drying (Bazzigher, Phytopath. Z., Volume 45, 53–56, 1962). Some ascomycetous and basidiomycetous fungi survived lyophilization, however, cultures were revived immediately after lyophilization, and the long-term survival of freeze-dried cultures was not evaluated. A nonsporulating strain of *Claviceps paspali* Stev. and Hull. remained viable for 3 years following lyophilization (Pertot et al., Eur. J. Appl. Microbiol., Volume 4, 289–294, 1977). While there are various methods for lyophilizing and storing fungi, there remains a need in the art for a method for extended preservation of mycorrhizal fungi, especially nonsporulating ericoid mycorrhizal fungi, in order to attain long-term storage of viable fungi for use in a system to promote the survival of ericaceous plants, especially micropropagated ericaceous plants. The present invention is different from related art methods and provides lyophilized mycorrhizal fungi and uses for the lyophilized fungi.

SUMMARY OF THE INVENTION

It is therefore an object of the present invention to provide a method for extending preservation of mycorrhizal fungi for long-term storage using lyophilization.

A further object of the present invention is to provide lyophilized mycorrhizal fungi.

A further object of the present invention is to provide a system for inoculating ericaceous plants with mycorrhizal fungi which have been lyophilized.

Another object of the present invention is to provide a method for improving survival of ericaceous plants including adding lyophilized ericaceous fungi to soil containing ericaceous plants.

Another object of the present invention is to provide a system for inoculating micropropagated ericaceous plants with mycorrhizal fungi which have been lyophilized.

Another object of the present invention is to provide a soilless system for inoculating micropropagated ericaceous plants with mycorrhizal fungi which have been lyophilized wherein the system includes a 1:1 peat:vermiculite (V:V) mixture with amended Woody Plant Medium and lyophilized fungi.

A further object of the present invention is to provide a method for improving survival of micropropagated ericaceous plants including incubating the plants in a soilless medium that includes ericoid mycorrhizal fungi which have been lyophilized.

A still further object of the present invention is to provide micropropagated plants that have been incubated in a soilless medium that includes ericoid mycorrhizal fungi which have been lyophilized.

Further objects and advantages will become apparent from the following disclosure.

DETAILED DESCRIPTION OF THE INVENTION

Plants in the Ericaceae include many commercially important species such as, for example, in fruit crops, blueberry and cranberry (Vaccinium spp); and important ornamentals such as rhododendron and azalea (Rhododendron spp.). Mountain andromeda, for example, an ericaceous plant native to western North Carolina, has desirable ornamental characteristics but its commercial potential in the landscape plant industry is limited by poor survival of micropropagated plants after they are transplanted to open containers. In nature, roots of plants in this family are infected by ericoid mycorrhizal fungi that improve the mineral and water-absorbing abilities of the plants. To date, application of lyophilization for the preservation of nonsporulating ericoid mycorrhizal fungi, subsequent to long-term storage of cultures, and preparation of inoculum has not been achieved. The present invention presents a method for lyophilization which is effective in maintaining viability of nonsporulating and sporulating strains of fungi.

The method of this invention is applicable to the preservation of any fungi, especially ericoid mycorrhizal fungi that are useful for growing ericaceous plants. Ericoid fungi include, for example, species of Hymenoscyphus, Oidiodendron; especially *Hymenoscyphus ericae, Oidiodendron griseum, Oidodendron maius*, etc.

Specifically, the method of the present invention is useful for lyophilization and storage of ericoid mycorrhizal fungi since this permits standardized and practical use of these fungi. USes include, for example, facilitating growth of ericaceous plants, especially facilitating acclimatization and growth of micropropagated ericaceous plants. Lyophilization is effective in maintaining viability of nonsporulating strains of *Hymenoscyphus ericae* and sporulating strains of Oidiodendron spp. up to at least one year from lyophilization when stored at −80° C. under normal atmospheric gases. Storage at about 4° C. or −20° C. results in the greatest long-term viability. Room temperature, about 23° C., results in rapid loss of viability in one of two strains of *H. ericae* tested. Lyophilized strains of *H. ericae* are capable of forming typical ericoid mycorrhizae with roots of seedlings of ericaceous plants following successful rehydration and revival in vitro. Colonized seedlings exhibit increased growth over noninoculated controls indicating the fungi retain mycorrhiza-forming ability throughout lyophilization and long-term storage. Lyophilization of ericoid mycorrhizal fungi is an effective method for preserving these endophytes.

Lyophilization is defined as a procedure for preservation of viable biological cultures by drying them in a frozen state under a vacuum by sublimation of ice. For the purposes of this invention, lyophilization removes not only about 90% of water sequestered as ice prior to sublimation, but most of the bound water within the cells as well. Residual moisture contents are usually about 1% to about 3%, of the original weight of the cells. Preserving cell viability by lyophilizing (freeze-drying) is based on liquid water being essential for active biological processes. Reduced liquid water present in a cell during storage results in decreased biological activity and thus, greater potential for stability during long-term storage.

The majority of previous studies suggest that spores are required for fungal preservation by lyophilization techniques (Dalpé, In: Proceedings of the Seventh North American Conference on Mycorrhiza, Sylvia et al.-eds., page 279, 1987; Marx and Daniel, Canad. J. Microbiol., Volume 22, 338–341, 1976; Smith and Onions, In: The Preservation and Maintenance of Living Fungi, 1983). To date, few published reports have described protocols for freeze-drying fungal hyphae and successful revitalization of these cultures. The present invention demonstrates that nonsporulating and sporulating fungi survive lyophilization and retain the ability to form mycorrhizae.

In addition, although peat-based inocula have been proposed for both arbuscular (Graham, In: Proceeding of the 6th North American Conference on Mycorrhizae, Molina-ed., 1985) and ericoid mycorrhizal fungi (Bagyaraj, In: Beneficial Fungi and their Utilization, Nair et al.-eds., 59–84, 1986; Jeffries and Dodd, In: Handbook of Applied Mycology. Soil and Plants., Volume 1, 155–185, Arora et al.-eds., 1991), the present invention of lyophilizing the inoculum in a peat-based medium provides a simple, ready-to-use inoculum for ericaceous plants, especially for in vitro techniques for horticultural use.

The lyophilized fungi of the present invention are useful in a system for inoculating micropropagated ericaceous plants with mycorrhizal fungi which includes a soilless growing medium. Ericaceous plants include, for example, blueberries, cranberries, rhododendrons, azaleas, mountain laurel, etc.

In one preferred embodiment, fungal samples are cultured on fresh agar for approximately one month before subculturing or until a mass is obtained which can be subcultured. For ericoid fungi, fresh malt agar is used at a pH of approximately 5.2 to 5.7, pH of about 5.5 is preferred. The agar plates are sealed using any appropriate means such as PARAFILM®, for example. Any appropriate sealing means is defined as a sealer which is relatively water impermeable yet permits some gas exchange. The plates are placed in a controlled environment chamber at a temperature suitable for the particular fungi. For ericoid fungi, a suitable range of temperatures is about 20° C. to about 26° C., with approximately 23° C. preferred. The fungi are cultured for at least about one month or until the medium is exhausted. For ericoid fungi, they are grown for approximately one to two months, with one month preferred.

A sterile plug of approximately 0.2 to 1.0 cm$^3$, approximately 0.5 cm$^3$ preferred, is removed from the culture margins. The plug can be removed from any area of the culture, the preferred area is the margin which has the most metabolically active hyphae. The plugs are transferred aseptically to sterile cryogenic vials, preferably with screw caps, and the caps secured.

Vials are placed directly into liquid nitrogen without submersion in order to cool the vials to approximately –196° C. This takes approximately thirty seconds with a 0.5 cm$^3$ plug. Vials are then placed at approximately –76° C. and caps loosened for subsequent air exchange and venting for sublimation of ice/water vapors during lyophilization. The samples also can be held in liquid nitrogen until placement in the lyophilizer. However, dry ice is preferred for this step. The vials are then transferred to a lyophilizer that is pre-cooled to about –40° C. preferred for ericoid fungi. The lyophilization chamber is sealed and evacuated to about $10^{-1.22}$ mm Hg. After about 24 hours, the shelf temperature is increased to about –20° C. for about an additional 24 hours. Over about the next approximately 48 hours, the shelf temperature is increased about 20° C., about every 24 hours, until a shelf temperature of about +20° C. is reached. At this point, the chamber is vented slowly so that ambient atmospheric pressure is achieved after about 15 minutes. The vials are removed, capped tightly and sealed with a sealing material such as, for example, PARAFILM®. Vials are placed immediately on dry ice for transfer to a storage temperature appropriate for the fungi which is lyophilized. Ericoid fungi are stored from about 4° C. to about –80° C., with a preferred range of 4° C. to about –20° C.

Another preferred embodiment is to lyophilize fungi in soilless media for facilitating its use for growing micropropagated plants, especially ericaceous plants. In this embodiment, all steps are done under aseptic conditions. The soilless medium consists of sterilized peat:vermiculite (1:1; v:v) supplemented with about 3 ml of Woody Plant Medium supplemented with approximately 200 mg/liter NaH$_2$PO$_4$, approximately 80 mg/liter adenine hemisulfate and approximately 5 grams/liter sucrose, pH of about 5.2. Approximately 10 cm$^3$ of the complete medium is added to glass vials which are suitable for using in a lyophilizer and cold storage such as for example, KIMBLE™ Opticlear® glass shell vials. The medium is then inoculated with about a 2 mm$^2$ weft of hyphae/10 cm$^3$ of medium removed from the surface of fungi cultures that are actively growing. For species of Hymenoscyphus, it is preferred this culture be approximately one month old.

The vials are capped and sealed as described above in the first embodiment and placed in a controlled-environment chamber maintained at about 20–26° C., 23° C. preferred. After the fungal isolates have grown throughout the soilless medium, a sealing material such as PARAFILM® is removed and the bases of the vials are immersed into liquid nitrogen as described above in the first embodiment. This takes approximately thirty seconds with a 0.5 cm$^3$ plug. Vials are then placed at approximately –76° C. and caps loosened for subsequent air exchange and venting for sublimation of ice/water vapors during lyophilization. The samples also can be held in liquid nitrogen until placement in the lyophilizer. However, dry ice is preferred for this step. The vials are then transferred to a lyophilizer that is pre-cooled to about –40° C. The lyophilization chamber is sealed and evacuated to about $10^{-1.22}$ mm Hg. After about 24 hours, the shelf temperature is increased to about –20° C. for about an additional 24 hours. Over about the next approximately 48 hours, the shelf temperature is increased about 20° C., about every 24 hours, until a shelf temperature of about +20° C. is reached. At this point, the chamber is vented slowly so that ambient atmospheric pressure is achieved after about 15 minutes. The vials are removed, capped tightly and sealed with a sealing material such as, for example, PARAFILM®. Vials are placed immediately on dry ice for transfer to a storage temperature appropriate for the fungi which is lyophilized. Ericoid fungi lyophilized in the soilless medium are stored from about 4° C. to about –80° C., with a preferred range of 4° C. to about –20° C.

The following examples are intended to further illustrate the invention and are not intended to limit the scope of the invention as defined by the claims. Propagation of *Pieris floribunda* is used only as a test model for showing propagation of micropropagated ericaceous plants using lyophlized soilless medium containing ericoid mycorrhizal fungi which have been lyophilized by the method of the present invention. Any ericaceous plant, especially micropropagated plants, can be propagated using the present invention. Furthermore, the lyophilized ericaceous fungi can be used in any method using ericaceous fungi.

EXAMPLE 1

*Hymenoscyphus ericae* (HE) (ATCC 32985, American Type Culture Collection, Rockville, Md.), DA and LPA (Lemoine et al. 1992, supra), *Oidiodendron griseum* Robak (OG) (ATCC 60377), *Oidiodendron maius* Barron (OM) (ATCC 66504) and isolate C1 (a putative Oidiodendron sp. isolated from roots of wild-collected *Pieris floribunda* (Pursh)Benth. and Hook [(Mountain andromeda) see Starrett et al., Proc. Southern Nurserymen's Assoc., Res. Conf., 40th Annual Report, 239–242, 1996, herein incorporated by reference in its entirety], were transferred to 60×15 mm sterile, polystyrene petri dishes containing fresh malt agar (Difco Laboratories, Detroit, Mich.), approximately pH 5.5. The dishes were sealed with PARAFILM "M"® (American National Can, Greenwich, Conn.) and placed in a controlled-environment chamber at approximately 23° C. with a 16 hour photoperiod provided by two cool-white fluorescent lamps suspended about 24 cm above the plates. The lamps provided a photosynthetic photon flux (PPF) (400–700 mm) of ≈42 $\mu mol \cdot m^{-2} \cdot s^{-1}$ as measured at the tops of plates. These and all other light measurements were recorded with a LI-COR LI-185A quantum/radiometer/photometer (LI-COR, Lincoln, Neb.). Cultures were grown one month, and then a sterile cork borer was used to remove about a 0.5 cm³ plugs from colony margins. All isolates of Oidiodendron (*O. griseum, O maius* and isolate C1), were sporulating so actively growing satellite colonies were selected from these plates. Plugs were transferred aseptically to 2-ml sterile, NALGENE™ cryogenic screw cap vials (one plug per vial; Nage Nuncl Intl., Rochester, N.Y.), and the caps secured.

Vials were placed directly into liquid nitrogen, but not completely submersed. After immersion of vials for approximately 30 seconds, the vials had cooled to approximately −196° C. Vials were then placed on dry ice and maintained at approximately −76° C. The vial caps were loosened to provide air exchange and venting for sublimation of ice/water vapor, and vials were placed on shelves pre-cooled to approximately −40° C. in a lyophilizer (Trivac Model D16A, the Virtis Co., New York, N.Y.). It was not necessary to regulate the increase in sample temperature from about −196° C. to −76° C. and from about −76° C. to the shelf temperature of about −40° C. The lyophilization chamber was sealed and evacuated to about $10^{-1.22}$ mm Hg. After about 24 hours at approximately −40° C., the shelf temperature was increased to about −20° C. for about an additional 24 hours. For about the next 48 hours, shelf temperature was increased about 20° C. every 24 hours until a shelf temperature of about +20° C. was reached. Once samples had reached +20° C., the chamber was vented slowly so that ambient atmospheric pressure was achieved after about 15 minutes. The vials were removed, capped tightly and sealed with PARAFILM®. PARAFILM® is relatively water impermeable yet permits some gas exchange. Vials were placed immediately on dry ice until transfer to a −80° C. freezer for storage. After about 1 week, one sample of each fungal isolate was removed from the −80° C. freezer and warmed to ambient room temperature (approximately 23° C.). Vials were unsealed and the freeze-dried plugs were transferred aseptically, mycelial side down, onto fresh malt agar plates. Plates were sealed with PARAFILM® and placed in a controlled environment chamber at about 23° C. Hyphal growth was observed for all isolates within about two weeks from plating. After verifying that all samples survived lyophilization, three vials per isolate were removed from −80° C. storage at 2,4,8 or 12 months. At each evaluation time, samples were placed on malt agar and days until visible hyphal growth were recorded as described immediately above for the 1-week-old samples. After one month, cultures derived from lyophilized mycelia plated on malt agar were examined visually for characteristic morphological features.

Following lyophilization, elapsed time until new hyphae were visible on malt agar was variable for isolate HE and isolate DA over storage times. See Table 1 below. Isolate LPA, however, grew out consistently on malt agar approximately 7 days after plating. Isolate LPA had significantly faster regrowth across storage times than HE or DA at corresponding times.

Isolates OG, OM and C1 all grew on malt agar more quickly than HE, DA or LPA at each storage time (Table 1). After 8 or 12 months in storage, OM and C1 both produced hyphae visible on malt agar about 2 days after plating, exceeding the growth rate of OG at each time. Regardless of storage duration, each isolate developed morphological features characteristic of the isolate prior to lyophilization and storage. Isolates of Oidiodendron that were sporulating prior to lyophilization resumed sporulation after rehydration on malt agar.

EXAMPLE 2

In this example, *Hymenoscyphus ericae* was tested for its mycorrhizal capacity after in vitro culture on a peat-based medium, lyophilization in situ and subsequent storage. Two hundred seventy, 95×25 mm KIMBLE™ Opticlear® glass shell vials (Kimble Glass, Inc., Toledo, Ohio) were autoclaved for about 15 minutes at 121° C. Each vial contained approximately 10 cm³ of about 1 sifted peat:1 fine vermiculite (V/V) moistened with about 3 ml liquid Woody Plant Medium [WPM (Lloyd and McCown, Proc. Intl. Plant Prop. Soc., volume 30, 421–437, 1980; herein incorporated by reference)] supplemented with approximately 200 mg/l $NaH_2PO_4$, approximately 80 mg/l adenine hemisulfate and approximately 5 g/l sucrose. The medium was adjusted to a pH of about 5.2 prior to placement in vials. Vials were covered with 25 mm Magenta 2-way caps (Magenta Corp., Chicago, Ill.) and allowed to cool overnight in a laminar flow hood. Approximately 24 hours later, 90 vials containing the cooled peat:vermiculite medium were inoculated in a laminar flow hood with about 2 mm² wefts of hyphae removed from the surface of approximately one month old cultures of *H. ericae* (HE). Similarly, another 90 vials were inoculated with isolate DA, and 90 vials remained noninoculated (controls). After placement of the isolates in the vials, all vials were recapped and sealed with PARAFILM®.

Cultures were placed in a controlled environment chamber maintained at about 23° C. After about one month, the fungal isolates had grown throughout the peat:vermiculite medium in each inoculated vial. At this time, PARAFILM® was removed and the bases of the vials were immersed to a depth of approximately 2 cm into liquid nitrogen (approximately −196° C.) for about 30 seconds. Vials were then placed on dry ice (approximately −76° C.). The rate of cooling to −196° C. or the rate of warming from −196° C. to about −76° C. does not need to be regulated. Caps on the vials were loosened and vials placed on shelves pre-cooled to about −40° C. in a lyophilizer (Trivac model D16A, The Virtis Co., New York, N.Y.). There was no attempt to regulate the increase in sample temperature from about −76° C. to the shelf temperature of about −40° C. The chamber was sealed and evacuated to approximately $10^{-1.22}$ mm Hg. After about 24 hours at about −40° C., the shelf temperature was increased to approximately −20° C. and maintained at this temperature for about an additional 24 hours. For about the following two days, the shelf temperature was increased approximately 20° C. about every 24 hours until a shelf temperature of approximately +20° C. was attained. Once samples had reached about +20° C., the chamber was vented slowly so that ambient atmospheric pressure was achieved after approximately 15 minutes. Vials were removed and caps were secured tightly and sealed with PAPAFILM®. Vials were then transferred to one of three storage temperatures: approximately 23° C. (room), approximately 4° C. (refrigerator) or approximately −20° C. (freezer). Thirty vials of each inoculum, as well as thirty vials of noninoculated controls, were placed at each storage temperature and maintained in the dark. Vials were removed from each storage temperature at about 1, 4, 8 or 16 weeks. At every interval, five samples of each isolate were removed and placed in a laminar flow hood. At week 16 ten samples of each isolate were removed. The additional five samples were used to determine the moisture content of the medium (Bruce and Luxmore, IN: Method of Soil Analysis. Part 1: Physical and Mineralogical Methods. $2^{nd}$ ed., Klute-ed., 663–686, 1986; herein incorporated by reference).

Samples were allowed to acclimate to room temperature prior to removal of the PAPAFILM®. After PARAFILM® removal, caps were also removed and the contents of each vial were rehydrated with about 5 ml sterile, distilled water at room temperature. Once rehydrated, approximately 0.5 $cm^3$ of the peat:vermiculite medium was removed with a pair of sterile forceps and plated onto malt agar in 60×15-mm sterile, polystyrene petri dishes. Dishes were sealed with PARAFILM® and placed in a controlled-environment chamber at about 23° C. Cultures were examined visually each day for growth. Once hyphae were visible to the unaided eye, the number of days after plating was recorded. Samples plated on malt agar were also examined visually after a period of about one month to verify development of morphological characteristics for each isolate.

About ten days prior Lo removal of the vials from storage on each date, about 100 seeds of *P. floribunda* were surface-sterilized for about 15 minutes in aqueous 0.75% sodium hypochlorite and 0.05% Tween-20 [polyoxyethylene sorbitan monolaurate (Sigma Chem. Co., St. Louis, Mo.)]. Seeds were rinsed three times in sterile, distilled water and plated at approximately 10 seeds per dish, on water agar containing about 5 g/l tissue culture agar (JRH Biosciences, Lenexa, Kans.) in 60×15-mm sterile, polystyrene petri dishes. Dishes were sealed with PARAFILM® and placed in a controlled-environment chamber at about 23° C. with about a 16 hour photoperiod provided by two, cool-white fluorescent lamps suspended about 24 cm above dish level. The lamps provided a PPF of approximately 42 $\mu mol \cdot m^{-2} \cdot s^{-1}$ as measured at tops of dishes. Seedlings had fully expanded cotyledons at the time of rehydration of the lyophilized samples. Following removal of a portion of the peat:vermiculite medium for plating on malt agar, a seedling of *P. floribunda*, apparently free from contamination, was removed from the water agar and transferred aseptically to a vial containing the reconstituted peat:vermiculite (V:V) with fungi. One seedling was placed in each vial. Vials were recapped and sealed with PARAFILM™ and placed randomly in a 30 tube tray (Magenta Corp., Chicago, Ill.). Trays were placed in a controlled-environment chamber at about 23° C. with about a 16 hour photoperiod (PPF approximately 116 $\mu mol \cdot m^{-2} \cdot s^{-1}$) provided by four, cool-white fluorescent lamps suspended approximately 12 cm above cap level. Seedlings were incubated in the tubes for 1 month. Leaf number, seedling height, percent of root system colonized and intensity of root colonization were then quantified. Roots were cleared and stained (adapted by Brundrett et al. Can. Journ. Bot., Volume 62, 2128–2134, 1984) and examined by bright field microscopy. To determine percent root colonization, individual roots for each seedling were examined for the presence of cortical cells which were colonized. If a root had a cell colonized, the root was classified as "colonized". Intensity of colonization was determined by random selection of four colonized roots per seedling and counting the number of colonized cortical cells at 400× magnification using light microscopy (approximately 25–30 cells per observation).

The experimental design was a completely randomized design (CRD) with a three factor factorial arrangement of treatments. Data were subjected to analysis of variance procedures and means separated by the LSD test. In some cases, when fungi failed to revive, seedlings could not be evaluated for extent of root colonization or intensity of colonization because nonviable fungi did not penetrate roots. Therefore, missing values for these variables were entered creating unbalanced data. Unbalanced data were analyzed by appropriate methods [PROC GLM (SAS Institute Inc., 1990)].

A significant three-way interaction occurred among storage temperature, storage duration and fungal isolate for time to regrowth of fungal isolates plated on malt agar, percent root colonization and intensity of root colonization. Furthermore, a significant two-way interaction occurred between storage temperature and fungal isolates for seedling height measurements.

Increased duration of post-lyophilization storage lengthened the time required for rehydrated HE and DA to produce visible hyphae from the peat:vermiculite medium onto malt agar. See Table II below. Furthermore, HE stored at 23° C. required greater time to regrow than HE at 4° C. or −20° C. for corresponding rehydration periods. Time required for regrowth of HE stored at 4° C. and −20° C. was similar after short-duration storage (weeks 1 and 4) but regrowth was slower for samples at 4° C. than at −20° C. after longer storage periods (weeks 8 and 16). DA stored at 23° C. required greater time to regrow than DA at 4° C. or −20° C. for corresponding rehydration periods. Duration until regrowth of DA stored at 4° C. and −20° C. was similar at corresponding storage times (See Table II below).

Across all storage temperatures and durations, all lyophilized HE or DA grew from peat:vermiculite onto malt agar except when isolate HE was held at 23° C. for 8 or 16 weeks. After 8 weeks storage at room temperature, only two of five samples developed new hyphae and at 16 weeks, only one of five grew. Isolates DA and HE that revived retained morphological features characteristic of the original culture following rehydration regardless of storage duration or temperature.

Seedlings inoculated with lyophilized HE stored at 23° C. for one week had 100%, of root cortical cells colonized, whereas only 13% were colonized by lyophilized HE stored at room temperature for 16 weeks. See Table III below. Seedlings inoculated with isolate DA stored at 23° C., however, did not exhibit a reduction in ability to colonize roots despite extended (16 week) storage.

Ability of HE to colonize roots was significantly less after four weeks at 4° C. than after one week. Lyophilized DA also exhibited a significant reduction in the capacity to colonize roots of seedlings of *P. floribunda* after storage at 4° C. for 16 weeks. There was no significant decrease in the apparent ability of DA to colonize roots even after 16 weeks at 23° C. There was no significant decrease in root colonization by isolates HE or DA after storage at −20° C. regardless of storage duration (See Table III below).

Values for intensity of cell colonization in roots of seedlings of *P. floribunda* by HE and DA were somewhat variable. See Table IV below. Across all storage temperatures and storage durations, HE colonized about 1% to about 74% (mean=about 64%) of the root cells, and DA colonized about 43% to about 81% (mean=about 66%) of the root cells. After HE was stored 16 weeks at 23° C., the ability to colonize cells was nearly absent. In contrast, intensity of cell colonization by DA at 23° C. increased with storage duration. Roots inoculated with DA stored 16 weeks at 23° C.

had significantly greater cell colonization than seedlings inoculated with DA stored for 1 week (Table IV below). Seedlings inoculated with DA, stored at 23° C. for 1 week, had significantly fewer cells colonized than seedlings inoculated with DA at 4° C. or −20° C. for 1 week (Table IV below). Similarly, seedlings inoculated with DA, stored at 23° C. for 4 weeks, had significantly fewer cells colonized than seedlings inoculated with DA at either 4° C. or −20° C. for 4 weeks. After 8 weeks at 23° C., DA root colonization intensity was less than that of DA at −20° C. but not significantly from DA at 4° C.

Heights of seedlings of *P. floribunda* inoculated with HE or DA were significantly greater than heights of noninoculated control plants, regardless of storage temperature. See Table V below). Control seedlings (grown with noncolonized peat:vermiculite that had been lyophilized and stored) exhibited similar shoot growth regardless of storage temperature. Seedlings inoculated with lyophilized HE stored at 23° C. were significantly taller than seedlings grown in vials containing HE stored at 4° C. or −20° C. Similarly, seedlings inoculated with DA stored at 23° C. were taller than seedlings grown in vials containing cultures of DA at 4° C. or −20° C. Seedlings inoculated with HE stored at 4° C. were similar in size to seedlings inoculated with DA stored at the same room temperature. Likewise, seedlings inoculated with HE stored at −20° C. were similar in size to seedlings inoculated with DA stored at the same temperature. Seedlings inoculated with DA had slightly greater shoot height than seedlings inoculated with isolate HE when lyophilized isolates were stored at 23° C. These results demonstrate that nonsporulating *H. ericae* can survive lyophilization and retain the ability to form mycorrhizae.

TABLE I

Time (days) until visible regrowth of lyophilized cultures of ericoid mycorrhizal fungi on malt agar after extended storage at −80° C.[a]

| Storage (months) | Fungal isolates[b] | | | | | |
|---|---|---|---|---|---|---|
| | HE | DA | LPA | OG | OM | Cl |
| 2 | 12.3 | 13.0 | 7.3 | 4.0 | 4.0 | 4.3 |
| 4 | 8.3 | 8.0 | 7.0 | 4.0 | 4.0 | 2.0 |
| 8 | 11.3 | 12.0 | 6.7 | 3.0 | 2.0 | 2.0 |
| 12 | 8.3 | 9.0 | 6.7 | 4.0 | 2.0 | 2.0 |

[a]Least Significant Difference ($LSD_{0.05}$) = 1.0 for mean comparison within columns or rows.
[b]HE = *Hymenoscyhus ericae* (ATCC), DA = putative *H. ericae*, isloate from INRA-CNRS, Dijon Cedex, France, LPA = *H. ericae*, isolate from INRA-CNRS, Dijon Cedex, France, OG = *Oidiodendron griseum* (ATCC), OM = *Oidiodendron maius* (ATCC), Cl = putative *Oidiodendron* sp., isolated from roots of wild-collected *Pieris floribunda* growing in North Carolina.

TABLE II

Days until regrowth following rehydration of lyophilized cultures of ericoid mycorrhizal fungi.[a]

| | | | | Storage temperatures | | | | | |
|---|---|---|---|---|---|---|---|---|---|
| | 23° C. (room) | | | 4° C. (refrigerator) | | | −20° C. (freezer) | | |
| Storage (weeks) | Control[c] | Isolates[b] HE | DA | Control | Isolates HE | DA | Control | Isolates HE | DA |
| 1 | = | 5 | 4 | = | 2 | 3 | = | 2 | 3 |
| 4 | = | 12 | 5 | = | 3 | 3 | = | 3 | 3 |
| 8 | = | 13 | 10 | = | 4 | 4 | = | 3 | 5 |
| 16 | — | 16 | 13 | — | 8 | 7 | — | 7 | 7 |

[a]Least Significant Difference ($LSD_{0.05}$) = 1 for mean comparison within columns, rows or between corresponding cells of the storage temperatures.
[b]HE = *Hymenoscyphus ericae*, DA = putative isolate of *H. ericae*.
[c]Controls had no fungus present, therefore, missing values were used.

TABLE III

Percentage of roots colonized in seedlings of *Pieris floribunda* by lyophilized ericoid mycorrhizal fungi stored at selected temperatures for 1 to 16 weeks.[a]

| | | | | Storage temperatures | | | | | |
|---|---|---|---|---|---|---|---|---|---|
| | 23° C. (room) | | | 4° C. (refrigerator) | | | −20° C. (freezer) | | |
| Storage (weeks) | Control[c] | Isolates[b] HE | DA | Control | Isolates HE | DA | Control | Isolates HE | DA |
| 1 | = | 100.0 | 100.0 | = | 97.6 | 98.8 | = | 97.2 | 88.6 |
| 4 | = | 97.6 | 96.0 | = | 87.8 | 98.0 | = | 97.6 | 98.6 |
| 8 | = | 77.5 | 97.0 | = | 78.8 | 93.4 | = | 90.0 | 94.4 |
| 16 | — | 13.0 | 97.8 | — | 88.0 | 84.2 | — | 89.2 | 92.8 |

[a]Least Significant Difference ($LSD_{0.05}$) = 7.9 for mean comparison within columns, rows or between corresponding cells of the three storage temperatures.
[b]HE = *Hymenoscyphus ericae*, DA = putative isolate of *H. ericae*.
[c]Controls had no fungus present, therefore, missing values were used.

TABLE IV

Intensity (as a percentage) of cells colonized in colonized portions of roots of seedlings of *Pieris floribunda* by lyophilized ericoid mycorrhizal fungi stored at selected temperatures for 1 to 16 weeks.[a]

| Storage (weeks) | 23° C. (room) | | | 4° C. (refrigerator) | | | −20° C. (freezer) | | |
|---|---|---|---|---|---|---|---|---|---|
| | Control[c] | Isolates[b] HE | DA | Control | Isolates HE | DA | Control | Isolates HE | DA |
| 1  | = | 61.0 | 42.8 | = | 67.2 | 68.4 | = | 73.8 | 69.0 |
| 4  | = | 67.4 | 48.4 | = | 56.8 | 81.2 | = | 72.6 | 69.4 |
| 8  | = | 73.5 | 56.2 | = | 63.4 | 66.6 | = | 58.6 | 72.2 |
| 16 | — | 1.0  | 73.6 | — | 65.4 | 67.6 | — | 62.4 | 79.4 |

[a]Least Significant Difference ($LSD_{0.05}$) = 13.7 for mean comparison within columns, rows or between corresponding cells of the three storage temperatures.
[b]HE = *Hymenoscyphus ericae*, DA = putative isolate of *H. ericae*.
[c]Controls had no fungus present, therefore, missing values were used.

TABLE V

Heights (cm) of seedlings of *Pieris floribunda* 1 month following inoculation with ericoid mycorrhizal fungi, lyophilized and stored at one of three temperatures.[a]

| Storage temperature (°C.) | Fungal isolates[b] | | |
|---|---|---|---|
| | Control (noninoculated) | HE | DA |
| 23 (Room) | 1.1 | 2.8 | 3.2 |
| 4 (Refrigerator) | 0.8 | 2.2 | 2.0 |
| −20 (Deep freeze) | 0.8 | 2.2 | 2.1 |

[a]Least Significant Difference ($LSD_{0.05}$) = 0.3 for mean comparison within columns or rows.
[b]Control = noninoculated, HE = *Hymenoscyphus ericae*, DA = putative isolate of *H. ericae*.

The forgoing description is for the purpose of illustration. Others skilled in the art can apply the knowledge described to lyophilization of select mycorrhizal fungi and to the use of these stored fungi for growing and/or acclimatizing their respective host plant. Furthermore, the lyophilized fungi can be used in any procedure that requires viable fungi. Such detail is solely for that purpose and those skilled in the art can make variations therein without departing from the spirit and scope of the invention.

We claim:

1. Lyophilized Hymenoscyphus fungi.

2. A sterile, lyophilized plant growth medium comprising a soilless medium containing lyophilized Hymenoscyphus fungi.

3. A system for growing ericaceous plants comprising a soilless medium, effective amounts of a lyophilized Hymenoscyphus fungi to facilitate the growth and/or the acclimatization of said ericaceous plants, and a container.

4. The system of claim 3 further comprising a micropropagated ericaceous plant.

5. The system of claim 4 wherein said plant is selected from the group consisting of blueberry, cranberry, rhododendron, azalea and andromeda.

6. A method for lyophilizing Hymenoscyphus fungi comprising:
   (a) placing a precooled sample of Hymenoscyphus fungi into a precooled lyophilizer,
   (b) evacuating said lyophilizer,
   (c) increasing said lyophilizer to about −20° C. after about 24 hours,
   (d) increasing said lyophilizer by about 20° C. about every 24 hours to reach a shelf temperature of about +20° C.,
   (e) venting the chamber of said lyophilizer, and
   (f) removing said fungi.

7. The method of claim 6 further comprising storing the lyophilized fungi at about 4° C. to about −80° C.

8. The method of claim 6 wherein said fungi are lyophilized as a sterile plug removed from an agar culture.

9. The method of claim 6 wherein said fungi are lyophilized in a soilless plant growth medium.

10. The method of claim 7 wherein said fungi are lyophilized as a sterile plug removed from an agar culture.

11. The method of claim 7 wherein said fungi are lyophilized in a soilless plant growth medium.

12. A Hymenoscyphus fungi produced by the method of claims 6, 7, 8, 9, 10, or 11.

13. A method for inoculating micropropagated ericaceous plantlets with Hymenoscyphus fungi comprising:
   (a) reconstituting a soilless medium containing lyophilized Hymenoscyphus fungi using water,
   (b) planting micropropagated ericaceous plantlets in said reconstituted medium, and
   (c) incubating micropropagated plantlets in order to establish colonization of said fungi on plantlet roots.

* * * * *